United States Patent
Goby

(10) Patent No.: US 10,500,100 B2
(45) Date of Patent: Dec. 10, 2019

(54) WOUND DRESSING

(71) Applicant: Adhex Technologies, Chenove (FR)

(72) Inventor: Jean-Michel Goby, Sennecey les Dijon (FR)

(73) Assignee: Adhex Technologies, Chenove (FR)

( * ) Notice: Subject to any disclaimer, the term of this patent is extended or adjusted under 35 U.S.C. 154(b) by 1043 days.

(21) Appl. No.: 14/284,332

(22) Filed: May 21, 2014

(65) Prior Publication Data

US 2015/0005688 A1    Jan. 1, 2015

(30) Foreign Application Priority Data

May 22, 2013  (EP) ..................... 13168749

(51) Int. Cl.
*A61F 13/02*  (2006.01)
*A61F 13/00*  (2006.01)

(52) U.S. Cl.
CPC .... *A61F 13/0259* (2013.01); *A61F 13/00085* (2013.01); *A61F 13/0253* (2013.01); *A61F 13/0289* (2013.01); *A61F 2013/00289* (2013.01); *Y10T 83/0341* (2015.04)

(58) Field of Classification Search
CPC ............ A61F 13/00085; A61F 13/0253; A61F 13/0259; A61F 2013/00289
USPC ......... 602/54, 52, 58, 59; 128/858; 424/445, 424/448, 449
See application file for complete search history.

(56) References Cited

U.S. PATENT DOCUMENTS

| | | | |
|---|---|---|---|
| 2010/0318013 A1* | 12/2010 | Fabo | ............... A61F 13/023 602/54 |
| 2011/0253304 A1 | 10/2011 | Ohta et al. | |
| 2012/0308754 A1* | 12/2012 | Dehlinger | ........... A61F 13/0269 428/41.8 |

FOREIGN PATENT DOCUMENTS

| | | |
|---|---|---|
| WO | 0004348 A1 | 1/2000 |
| WO | 0033776 A1 | 6/2000 |
| WO | 2010134873 A1 | 11/2010 |

OTHER PUBLICATIONS

European Search Report (4 pages) dated Jun. 18, 2013 issued by the European Patent Office for priority application EP 13168749.3.

* cited by examiner

*Primary Examiner* — Ophelia A Hawthorne
*Assistant Examiner* — Caitlin A Carreiro
(74) *Attorney, Agent, or Firm* — Young & Thompson

(57) ABSTRACT

A wound dressing is provided that includes at least a support including a thin pliable film with a top face and a bottom face, a pressure-sensitive adhesive layer applied to at least a portion of the bottom face of the thin pliable film, a protective layer applied detachably to the pressure-sensitive adhesive layer opposite the support and an additional layer either in the form of a uniform layer such as a film, or in the form of a frame, covering the top face of the thin pliable film. At least a part of at least the thin pliable film is trimmed in such a way that a space is created between the additional layer and the thin pliable film, the space providing a beginning for the easy removing of the additional layer.

15 Claims, 3 Drawing Sheets

WOUND DRESSING

FIELD OF THE INVENTION

The invention relates to the field of dressings that are applied to skin, and more particularly, to the field of dressings having means for making the application of the dressing easier.

PRIOR ART

It is well known dressings with thin films, usually transparent, which are widely used as a protective layer over wounds since they facilitate healing in a moist environment, while acting as a barrier against liquids and contamination by bacteria. Said films are also used as surgical insice drapes because of their ability to act as a barrier against bacterial contamination. Said dressings usually comprise at least a support comprising a thin pliable film with a top face and a bottom face, a pressure-sensitive adhesive applied to at least a portion of the bottom face of the support and a protective layer applied detachably to the pressure-sensitive adhesive opposite the support. Such dressings are used notably in Vacuum-Assisted Closure (VAC), also called vacuum therapy, vacuum sealing or topical negative pressure therapy. Vacuum-Assisted Closure is a simple technique where a piece of foam with an open-cell structure is inserted into the wound, and a wound drain with lateral perforations is laid atop it. The entire area is then covered with a transparent adhesive membrane, which is firmly secured to the healthy skin around the wound margin. When the exposed end of the drain tube is connected to a vacuum source, fluid is drawn from the wound through the foam into a reservoir for subsequent disposal.

Nevertheless, when the protective layer is stripped off, the adhesive-coated film tends to crumple and stick to itself, thus preventing aseptic and gentle application of the dressing to the skin of a patient.

To overcome this problem, various systems for applying such dressings have been proposed. The principle of those various systems consists in adding to the coated film a additional layer of a rigid material either in the form of a uniform layer such as a film, or in the form of a frame, the rigid material facilitating positioning and being removed after the dressing has been applied to the skin.

It is the case, for example, of U.S. Pat. No. 4,372,303 that discloses a frame for spreading relatively large adhesive backed bandages into a generally flat configuration for applying to a patient. The system for bandaging a patient comprises a flexible bandage having a backing with an adhesive on a surface thereof for applying to a patient and a frame means which is substantially less flexible than the bandage and is attachable to the backing thereof for maintaining said bandage in a generally flat configuration and for controlling wrinkling during handling and application of the bandage to the patient when attached thereto, whereby the bandage may resume its flexible nature after application to the patient and removal of the frame means, so as not to interfere with the flexible functioning of the bandage on the patient's anatomy. Consequently, the frame is attached to the bandage when the bandage is being stuck to the patient, but the frame is removed so as not to interfere with subsequent movement of the patient's anatomy.

We also know the international patent application WO 9725012 that discloses a wound dressing having a film dressing layer which is coated with adhesive on one side. The dressing is supported in a flat, wrinkle-free condition by two edge portions of the adhesive protector layer and a support layer on the non-adhesive surface of the dressing layer. The protector edge portions include a part which extends beyond the edge of the dressing to serve as a tab or handle to facilitate its removal.

Nevertheless, while to a certain extent they are helpful for positioning, these dressings have several disadvantages.

The difference in rigidity between the thin film and additional layer that is adhesively bonded, thermobonded, or mechanically fastened onto the surface of the film opposite from its surface coated in adhesive gives rise, during removal of the additional layer, to a disturbance in the adhesive connection between the skin and the dressing. That may cause partial detachment of the dressing from the skin or the appearance of wrinkles that can result in premature failure of the adhesion of the dressing or in poor application.

Another drawback of these dressings is that they, after removal of the protective layer from the adhesive, they have a tendency to curl up, rendering positioning difficult.

Moreover, the thiner the dressings are, more aforementionned drawbacks are great. When said dressings are thiner, their pliability and adhesiveness make them more difficult to handle and therefore more difficult to apply. Very thin dressings are also more likely to stick to themselves during application becoming virtually useless and ultimately discarded. Furthermore, the additionnal layer is more difficult to remove after application of the dressing.

One additional problem associated with these complicated release systems becomes apparent when one considers that the human body essentially has no flat surfaces; it is comprised of many complex curves, i.e. surfaces which curve in more than one direction at the same time. Classic stiff release systems, many containing a plurality of release layers, work well on flat surfaces, but fail to aid in easily applying dressings to the complex curves of the human body in a wrinkle-free (e.g., having no parts folding onto each other or flat with no folds) manner. The failure to reliably aid in applying the dressing in a wrinkle-free manner ultimately compromises the ability of the dressing to protect the wound.

We also know the international patent application WO 2010/134873 that discloses a method of manufacturing a film dressing comprising the steps of feeding a composite web consisting of a first layer of thin plastic film and a second carrier layer relasably attached to the thin film, and a web of release material in a machine direction, applying a layer of adhesive onto the web of release material or onto the layer of thin plastic film, bringing together the composite web consisting of a first layer of thin plastic film with a second carrier layer and the web of release material after the layer of adhesive has been applied to either the web of release material or the layer of thin plastic film, cutting the web of release material along a line extending in the machine direction. The method includes the further step of weakening the first layer of thin film along a line coincident to the line cut in the web of release material. This document also discloses a film dressing comprising a thin plastic film, a stiffening layer releasably attached to one side of the plastic film, a layer of adhesive applied to the plastic film on the side opposite to the stiffening layer and a release sheet covering the adhesive layer, wherein a cutting line extending along an edge of the dressing at a determined distance therefrom is made through the release sheet. Moreover, a weakening line coincident to the cutting line in the release sheet is made in the plastic film. Nevertheless, this film dressing fails to reliably aid in applying the dressing in a wrinkle-free manner.

To overcome above-mentioned limitation, a need exists for a cheaper dressing that is easy to apply without contaminating the dressing during application and wherein the additionnal layer is easy to remove without damaging the dressing.

SUMMARY OF THE INVENTION

It is therefore an object of the invention to provide a dressing having a moderate cost and being easy to apply in very few steps, using a minimum of release layers, allowing the dressing's sterility to remain uncompromised, allowing the positioning of the dressing on the wound to be accomplished in a flat and wrinkle free manner on the complex curves of the human body and being easy to remove without damaging the dressing.

For this purpose, it is proposed a wound dressing comprising at least a support comprising a thin pliable film with a top face and a bottom face, a pressure-sensitive adhesive layer applied to at least a portion of the bottom face of the thin pliable film, a protective layer applied detachably to the pressure-sensitive adhesive layer opposite the support and a additional layer either in the form of a uniform layer such as a film, or in the form of a frame, covering the top face of the thin pliable film; said wound dressing is remarkable in that at least a part of at least the thin pliable film is trimmed in such a way that a space is created between the additionnal layer and the thin pliable film, said space providing a beginning for the easy removing of the additionnal layer.

In a first embodiment, the thin pliable film and the pressure-sensitive adhesive layer are trimmed.

In a second embodiment, the thin pliable film, the pressure-sensitive adhesive layer and the protective layer are trimmed.

Preferably, at least the thin pliable film is trimmed by forming at least one pre-cut line into said at least thin pliable film and by tearing off the thin pliable film along the pre-cut line.

Advantageously, the pre-cut line is obtained by performing a series of incisions into at least the thin pliable film.

Each incision of the pre-cut line has a length comprised between 0.5 mm and 3 mm and the space between two incisions is comprised between 1 mm and 3 mm.

Moreover, the thin pliable film is made of a material selected from the group consisting of polyurethane, polyethylene, polypropylene, styrene-isoprene copolymers, styrene-butadiene block copolymers, butadiene rubbers, isoprene rubbers, neoprene rubbers, acrylonitrile rubbers, silicone rubbers, butyl rubbers, chloroprene rubbers, polyvinylchloride, polyamides, foamed material and non-woven material, or mixtures thereof.

The protective layer is made of a material having an adhesive resistant surface on the dressing cover area and the film material selected from the group consisting of a plastic, PET, metalized plastic, foil and paper.

Said adhesive resistant surface is silicone-based.

Furthermore, the additional layer extends beyond the thin pliable film to provide at least a tab for ease in handling and application of dressing.

Another object of the present invention relates to a process for the production of a wound dressing comprising at least a support comprising a thin pliable film with a top face and a bottom face, a pressure-sensitive adhesive layer applied to at least a portion of the bottom face of the thin pliable film, a protective layer applied detachably to the pressure-sensitive adhesive layer opposite the support and a additional layer either in the form of a uniform layer such as a film, or in the form of a frame, coating the top face of the thin pliable film; said process is remarkable it comprises at least the following steps of forming at least one pre-cut line into at least the thin pliable film and tearing off the thin pliable film along the pre-cut lines to trimm at least the thin pliable film in such a way that a space is created between the additionnal layer and the thin pliable film, said space providing a beginning for the easy removing of the additionnal layer.

Said pre-cut line is obtained by performing a series of incisions into at the least thin pliable film.

In a first embodiment, the pre-cut line is formed into the thin pliable film and the pressure-sensitive adhesive layer.

In a second embodiment, the pre-cut line is formed into the thin pliable film, the pressure-sensitive adhesive layer and the protective layer.

Moreover, each incision of the pre-cut line has a length comprised between 0.5 mm and 3 mm and the space between two incisions is comprised between 1 mm and 3 mm.

Preferably, the thin pliable film is made of a material selected from the group consisting of polyurethane, polyethylene, polypropylene, styrene-isoprene copolymers, styrene-butadiene block copolymers, butadiene rubbers, isoprene rubbers, neoprene rubbers, acrylonitrile rubbers, silicone rubbers, butyl rubbers, chloroprene rubbers, polyvinylchloride, polyamides, foamed material and non-woven material, or mixtures thereof.

The protective layer is made of a material having an adhesive resistant surface on the dressing cover area and the film material selected from the group consisting of a plastic, PET, metalized plastic, foil and paper.

Said adhesive resistant surface is silicone-based.

DESCRIPTION OF THE DRAWINGS

For a further understanding of the objects and advantages of the present invention, references should be made to the following drawings in conjunction with the accompanying descriptions and operations, wherein.

DETAILED DESCRIPTION

It is emphasized that, in accordance with the standard practice in the industry, various features are not drawn to scale. In fact, the dimensions of the various features may be arbitrarily increased or reduced for clarity of discussion. Moreover, in the following description, the term "thin" means a film with a thickness of 15 µm (micrometer) to 70 µm and the term « pliable » or « flexible » means any material with sufficient conformability for it to adapt to curves on the body, such as joints for example, or a substrate such as catheters for example.

Figure 1:
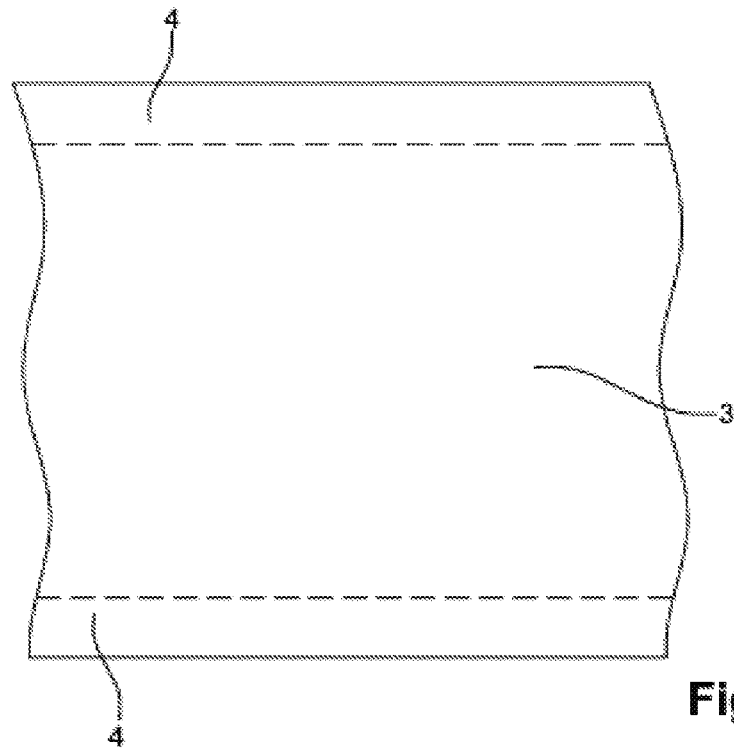
FIG. 1 is a top view of the wound dressing according to the invention.
Figure 2:
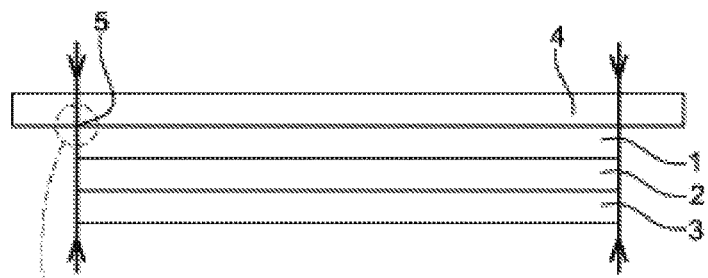
FIG. 2 is a schematic cross sectional view of the dressing of FIG. 1.
Figure 3:
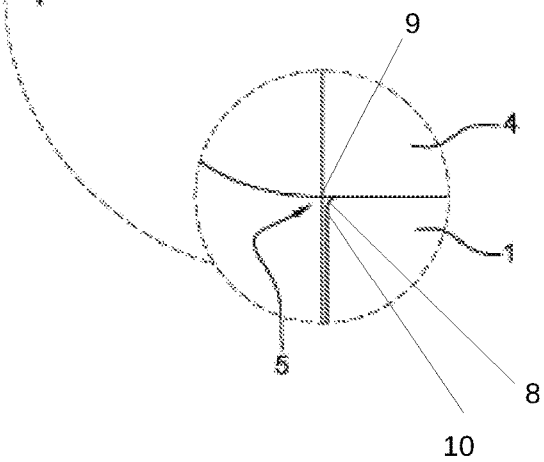
FIG. 3 is a detailed view of the cross sectional view of the dressing of FIG. 2 showing a space between the additionnal layer and the thin pliable film.

Referring to FIGS. 1 to 3, the wound dressing comprises at least a support comprising a thin pliable film (1) with a top face and a bottom face, a pressure-sensitive adhesive layer (2) applied to at least a portion of the bottom face of the thin pliable film (1), a protective layer (3) applied detachably to the pressure-sensitive adhesive layer (2) opposite the support and a additional layer (4) in the form of a uniform layer such as a film covering the top face of the thin pliable film (1).

It is obvious that said additional layer (4) could be in the form of a frame without departing from the scope of the invention.

The thin pliable film (1) is preferably made of a material selected from the group consisting of polyurethane, polyethylene, polypropylene, styrene-isoprene copolymers, styrene-butadiene block copolymers, butadiene rubbers, isoprene rubbers, neoprene rubbers, acrylonitrile rubbers, silicone rubbers, butyl rubbers, chloroprene rubbers, polyvinylchloride, polyamides, foamed material and non-woven material, or mixtures thereof.

The protective layer (3) may be one sheet covering the entire skin-contacting surface of the thin pliable film (1), or it may be split into one or more sections to provide a gripping surface during application. This gripping surface permits application without the need to touch the skin-contacting surface during application. The protective layer (3) may be made with any material having an adhesive resistant surface on the side of the protective layer (3) that contacts the skin-contacting surface of the thin pliable film (1).

The protective layer material should provide flexibility and make the sheet sufficiently rigid to protect the thin pliable film (1) portion it covers. In various example embodiments, the protective layer (3) is made of one, or a combination, of plastic, PET, paper, metallized plastic or foil. The adhesive resistant surface may be a layer of a silicone-based material applied to the film material.

The additional layer (4) may be sufficiently adhered to the thin pliable film (1) to provide a protective layer for the thin pliable film (1) as the dressing covers a wound site. The additional layer (4) is preferably made of a transparent material, similar to the thin pliable film (1) that allows a user to see the wound while the thin pliable film (1) covers the wound site. In some example embodiments, the additional layer (4) may be made of polyurethane, polyethylene, polypropylene, or mixtures, or combinations, thereof. The thickness of the additional layer (4) may be extremely thin to prevent imparting any rigidity to the thin-film dressing. Examples of the additional layer (4) may be about 20 to 50 mm thick. Commercially available thin pliable film (1) and additional layer (4) useful for the invention includes PLATILON U4101 XZ-T from BAYER MATERIEL SCIENCE which is a transparent polyester film including polyurethane (PU) and a liner in Polyethylen (PE) wherein the thichness is about 25 µm and the overall width is about 1250 µm.

The pressure-sensitive adhesive layer (2) can combine an adhesive material with a material having high moisture absorption properties. The adhesive material secures the thin pliable film (1) to the skin at the wound site. The adhesive material may include a tackifier, such as a hydrocarbon resin, and/or acrylic. In one example embodiment, the adhesive material comprises a combination of a tackifier and hot melt acrylic.

The highly moisture-absorbent material may be a hydrocolloid material. One example of a hydrocolloid that may be used is calcium carboxymethylcellulose ("CMC").

Others include pectin, gelatin, guar gum, high molecular weight carbowax, carboxypolymethylene, polyacrylate, polyvinyl alcohol, and polyvinyl pyrrolidone.

The tackifier can be a hydrocarbon resin and the elastomer can be a styrene-olefin-styrene polymers, but may also be polyisobutylene, natural rubber, silicone rubber, arcylonitrile rubber, and polyurethane rubber. The adhesive layer (3) may also include an extender, preferably paraffin oil. The extender may also be a material that functions as a plasticizer, particularly in combination with the elastomer. Such plasticizers include glycerin (glycerol), sorbitol, triethylene glycol. The extender may also be mineral oil, poly(butene 1) and polyisobutylene.

Referring to FIGS. 2 and 3, at least a part of at least the thin pliable film (1) is trimmed in such a way that a space (5) is created between the additional layer (4) and the thin pliable film (1), said space (5) providing a beginning for the easy removing of the additional layer (4). Said at least thin pliable film is trimmed by forming at least one pre-cut line (6) into said at least thin pliable film (1) and by tearing off an end portion (11) of the thin pliable film (1) along the pre-cut line (6) to result in a curved edge portion (8) of the thin pliable film (1) at an intersection (9) between the thin pliable film (1) and the additional layer (4), the space (5) being defined between the remaining outer edge (10) of the thin pliable film (1) after the end portion (11) is removed. Said pre-cut line (6) is obtained by performing a series of incisions into at least the thin pliable film (1). Each incision of the pre-cut line (6) has a length comprised between 0.5 mm and 3 mm and the space between two incisions is comprised between 1 mm and 3 mm. Said incisions can be made by any suitable means such as a disk with teeth for example.

It is obvious that the pre-cut line could be obtained by any suitable means well known by the man skilled in the art without departing from the scope of the invention.

Furthermore, referring to FIG. 2, the additional layer (4) extends beyond the thin pliable film (1) to provide at least a tab (7) for ease in handling and application of dressing.

Figure 4:
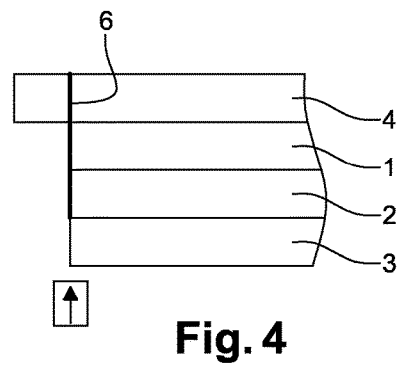
FIGS. 4 to 9 are schematic cross sectional views of different embodiment of the dressing according to the invention.
Figure 10:
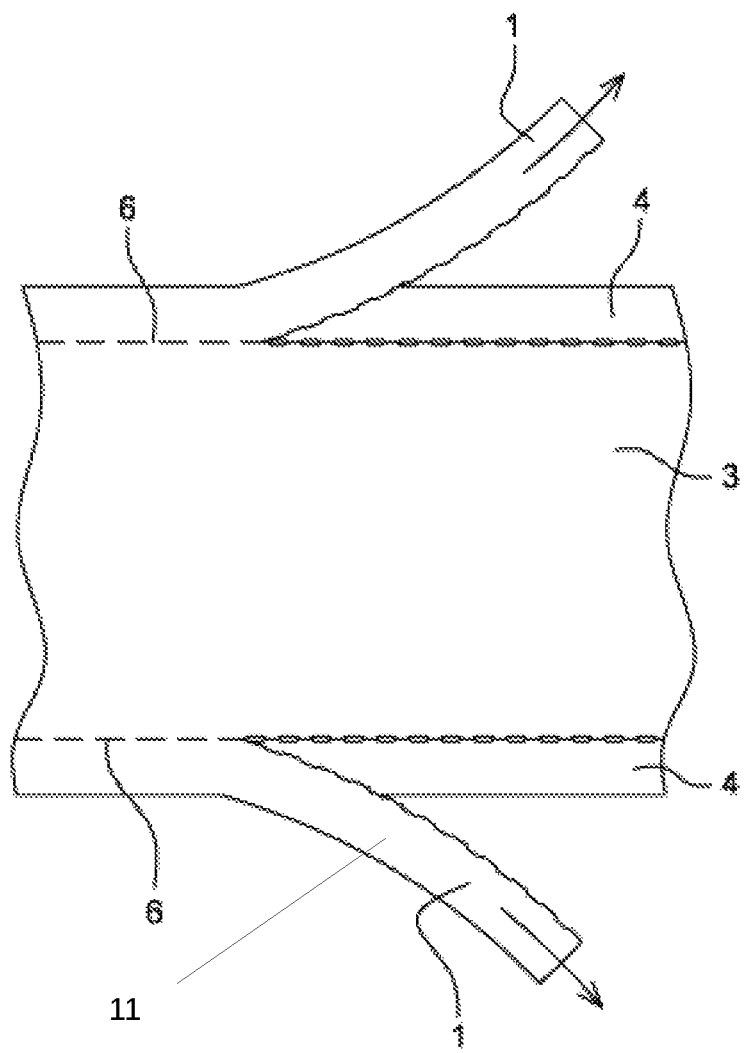
FIG. 10 is a top view of the wound dressing according to the invention showing the different steps of its process of production.

In a first embodiment, referring to FIG. 4, the wound dressing according to the invention is obtained by forming one pre-cut line (6) into the thin pliable film (1), the adhesive layer (2) and the additional layer (4) from the bottom face of the dressing and by tearing off the band (11) that is an end portion of thin pliable film (1) and the adhesive layer (2) along the pre-cut lines, as depicted in FIG. 10, to trim at least the thin pliable film (1).

Figure 5:
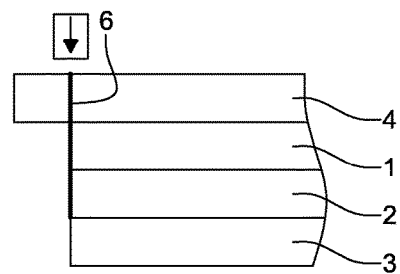

In a second embodiment, referring to FIG. 5, the wound dressing according to the invention is also obtained by forming one pre-cut line (6) into the thin pliable film (1), the adhesive layer (2) and the additional layer (4) from the top face of the dressing and by tearing off the band of thin pliable film (1) and the adhesive layer (2) along the pre-cut line (6), as depicted in FIG. 10, to trimm at least the thin pliable film (1).

Figure 6:
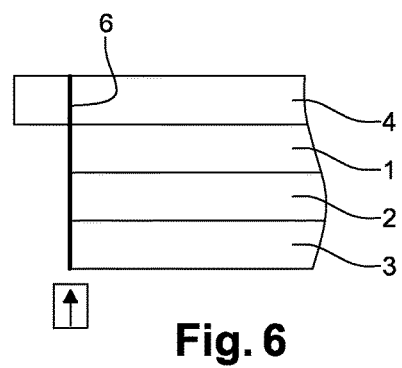

In yet another embodiment, referring to FIG. 6, the wound dressing according to the invention is obtained by forming one pre-cut line (6) into the thin pliable film (1), the adhesive layer (2), the protective layer (3) and the additional layer (4) from the bottom face of the dressing and by tearing off the band of all layers (1,2,3,4) along the pre-cut line (6), as depicted in FIG. 10, to trimm at least the thin pliable film (1).

Figure 7:
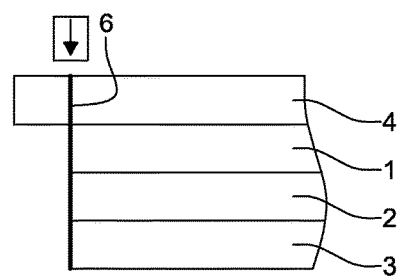

The embodiment shown on FIG. 7 differs from the preceeding embodiment of FIG. 6 by the fact that the pre-cut line (6) is made from the top face of the dressing.

Figure 8:
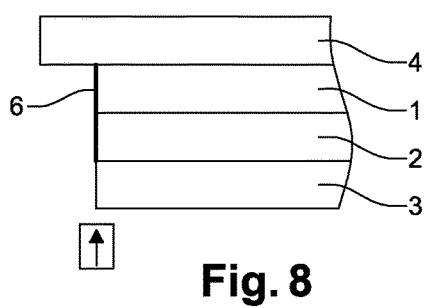

In yet another embodiment, referring to FIG. 8, the wound dressing according to the invention is obtained by forming one pre-cut line (6) into the thin pliable film (1) and the adhesive layer (2) from the bottom face of the dressing and by tearing off the band of thin pliable film (1) and the adhesive layer (2) along the pre-cut line (6), as depicted in FIG. 10, to trimm at least the thin pliable film (1).

Figure 9:
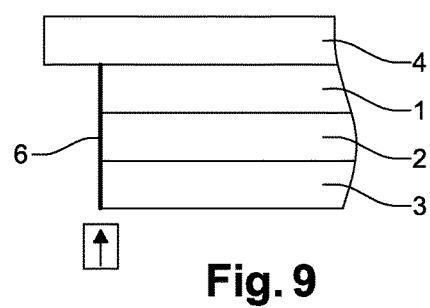

In a last embodiment, referring to FIG. 9, the wound dressing according to the invention is obtained by forming one pre-cut line (6) into the thin pliable film (1), the adhesive layer (2) and the protective layer (3) from the bottom face of the dressing and by tearing off the band of thin pliable film (1), adhesive layer (2) and protective layer (3) along the pre-cut line (6), as depicted in FIG. 10, to trimm at least the thin pliable film (1).

Although embodiments of the present disclosure have been described in detail, those skilled in the art should understand that they may make various changes, substitutions and alterations herein without departing from the spirit and scope of the present disclosure. Accordingly, all such changes, substitutions and alterations are intended to be included within the scope of the present disclosure as defined in the following claims. In the claims, means-plus-function clauses are intended to cover the structures described herein as performing the recited function and not only structural equivalents, but also equivalent structures.

I claim:

1. A wound dressing comprising:
   at least a support comprising a thin pliable film with a top face and a bottom face;
   a pressure-sensitive adhesive layer applied to at least a portion of the bottom face of the thin pliable film
   a protective layer applied detachably to the pressure-sensitive adhesive layer opposite the support;
   an additional layer that is one of a uniform layer and a frame, covering the top face of the thin pliable film, the additional layer extending beyond the thin pliable film to provide at least a tab for ease in handling and application of a dressing; and
   at least one pre-cut line formed into at least the thin pliable film, an end portion of the thin pliable film being configured to be torn at the at least one pre-cut line to result in a curved edge portion of the thin pliable film at an intersection between the thin pliable film and the additional layer, and at least a part of at least the thin pliable film is trimmed such that a layer space is defined between the additional layer and a remaining outer edge of the thin pliable film, after the end portion of the thin pliable film is torn along the pre-cut line,
   wherein said space provides a beginning for removing of the additional layer.

2. The wound dressing according to claim 1, wherein the pre-cut line is obtained by performing a series of incisions into at least the thin pliable film, and
   wherein an incision space separates two adjacent incisions.

3. The wound dressing according to claim 2, wherein each incision of the pre-cut line has a length between 0.5 mm and 3 mm, and the incision space between two incisions is between 1 mm and 3 mm.

4. The wound dressing according to claim 1, wherein the protective layer is made of a material having an adhesive resistant surface on a dressing cover area, and the film material selected from the group consisting of a plastic, PET, metalized plastic, foil, and paper.

5. The wound dressing of claim 4, wherein the adhesive resistant surface is silicone-based.

6. The wound dressing according to claim 1, wherein the thin pliable film and the pressure-sensitive adhesive layer are trimmed.

7. The wound dressing according to claim 1, wherein the thin pliable film, the pressure-sensitive adhesive layer, and the protective layer are trimmed.

8. The wound dressing of claim 1, wherein the thin pliable film is made of a material selected from the group consisting of polyurethane, polyethylene, polypropylene, styrene-isoprene copolymers, styrene-butadiene block copolymers, butadiene rubbers, isoprene rubbers, neoprene rubbers, acrylonitrile rubbers, silicone rubbers, butyl rubbers, chloroprene rubbers, polyvinylchloride, polyamides, foamed material and non-woven material, or mixtures thereof.

9. The wound dressing according to claim 1, wherein the uniform layer is a film.

10. A process for the production of a wound dressing including at least a support including a thin pliable film with a top face and a bottom face, a pressure-sensitive adhesive layer applied to at least a portion of the bottom face of the thin pliable film, a protective layer applied detachably to the pressure-sensitive adhesive layer opposite the support, and an additional layer that is one of a uniform layer and a frame, coating the top face of the thin pliable film, said process comprising at least the following steps:
    forming at least one pre-cut line into at least the thin pliable film; and
    tearing off an end portion of the thin pliable film along the pre-cut line to result in a curved edge portion of the thin pliable film at an intersection between the thin pliable film and the additional layer, and to trim at least the thin pliable film such that a layer space is defined between the additional layer and a remaining outer edge of the thin pliable film, said space providing a beginning for removing of the additional layer.

11. The process according to claim 10, wherein the at least one pre-cut line is obtained by performing a series of incisions into at least the thin pliable film.

12. The process according to claim 11, wherein each incision of the at least one pre-cut line has a length between 0.5 mm and 3 mm and the space between two incisions is between 1 mm and 3 mm.

13. The process according to claim 10, wherein the at least one pre-cut line is formed into the thin pliable film and the pressure-sensitive adhesive layer.

14. The process according to claim 10, wherein the at least one pre-cut line is formed into the thin pliable film, the pressure-sensitive adhesive layer, and the protective layer.

15. The process according to claim 10, wherein the uniform layer is a film.

* * * * *